(12) United States Patent
Nakagawa et al.

(10) Patent No.: US 7,989,588 B2
(45) Date of Patent: Aug. 2, 2011

(54) CELL PERMEABLE PEPTIDE

(75) Inventors: Shinsaku Nakagawa, Suita (JP);
Tadanori Mayumi, Kobe (JP); Kiichi Fukui, Suita (JP)

(73) Assignees: Osaka University, Osaka (JP); Nitto Denko Corporation, Osaka (JP)

( * ) Notice: Subject to any disclaimer, the term of this patent is extended or adjusted under 35 U.S.C. 154(b) by 1029 days.

(21) Appl. No.: 11/883,810

(22) PCT Filed: Feb. 9, 2006

(86) PCT No.: PCT/JP2006/302255
§ 371 (c)(1),
(2), (4) Date: Aug. 7, 2007

(87) PCT Pub. No.: WO2006/085583
PCT Pub. Date: Aug. 17, 2006

(65) Prior Publication Data
US 2011/0045009 A1    Feb. 24, 2011

(30) Foreign Application Priority Data
Feb. 10, 2005   (JP) .................................. 2005-035290

(51) Int. Cl.
*C07K 7/08* (2006.01)
*C07K 19/00* (2006.01)
*A61K 47/48* (2006.01)

(52) U.S. Cl. ......... 530/326; 530/327; 514/1.3; 435/69.7
(58) Field of Classification Search .................... None
See application file for complete search history.

(56) References Cited

U.S. PATENT DOCUMENTS
2003/0113819 A1   6/2003   Horton et al.

FOREIGN PATENT DOCUMENTS
| JP | H10-33186 A | 2/1998 |
| JP | 2001-199997 A | 7/2001 |
| WO | WO 94/04686 A | 3/1994 |
| WO | WO01/41811 | 6/2001 |

OTHER PUBLICATIONS

Suzuki et al., "Characteristics of Membrane Permeable Arginine-Rich Peptides," *Peptide Sequence 2000*, The Japanese Peptide Society, pp. 89-92.

*Primary Examiner* — Elly-Gerald Stoica
(74) *Attorney, Agent, or Firm* — Fitch, Even, Tabin & Flannery

(57) ABSTRACT

The number of peptides having an ability to bind to a cell or penetrate into a cell is narrowed down by being selectively enriched from a random peptide library with a diversity of not less than one hundred millions of peptides using a phage surface display technique, and then cytoplasmic transfer is evaluated by using protein synthesis inhibition as an indicator by adding to a cell, a fusion body of the selectively enriched peptide and a protein synthesis inhibitory factor (PSIF) that cannot solely penetrate into the cell.

5 Claims, 7 Drawing Sheets

CELL PERMEABLE PEPTIDE

This Application is the U.S. National Stage Application under 35 U.S.C. 371 of International Application PCT/JP/ 2006/302255 filed Feb. 9, 2006, which claims benefit from Japanese Patent Application No. 2005-35290 filed Feb. 10, 2005, the complete disclosures of which, including any and all sequence listings, are incorporated herein by reference.

TECHNICAL FIELD

The present invention relates to a peptide having a permeability into a cell and a peptide conjugate linking the peptide and a physiologically active substance. The present invention also relates to a vaccine, a formulation for percutaneous absorption, and in particular a tape formulation for the percutaneous absorption comprising the peptide or the peptide conjugate.

BACKGROUND ART

In recent years, several functional peptides (PTD: protein transduction domain) having an ability to penetrate into a cell have been identified, and attempts to develop PTD as an effective DDS (drug delivery system) carrier for percutaneous or permucosal absorption or brain delivery of a nucleic acid or a protein have been noticed. For example, the peptide/ protein has been tried to be introduced into the cell using peptides derived from HIV-1 Tat protein in Patent document 1. However, these PTD are poor in cell specificity and insufficient in introducing efficiency of proteins into the cell. Thus, it is essential to improve existing PTD and identify novel PTD. From this point of view, a cationic amino acid introduction body has been produced worldwide by peptide synthesis with trials and errors for the purposes of making analogues and enhancing an adsorption to the cell based on conformational analyses of PTD. However, diversity of peptides capable of being synthesized is limited, and no PTD superior to the TAT peptide has been found yet.

Patent document 1: Unexamined Japanese Application H10-33186.

DISCLOSURE OF THE INVENTION

Problems to be Solved by the Invention

Accordingly, it is one object of the present invention to provide a peptide which permeates into a cell more efficiently than TAT peptide (Tat 48-60), and a peptide conjugate linking the peptide and a physiologically active substance having a poor cell permeability.

It is another object of the present invention to provide a pharmaceutical composition and a formulation for percutaneous absorption comprising a vaccine comprising the peptide or a conjugate thereof.

Further, it is another object of the present invention to introduce a physiologically active substance into a cell by taking advantage of the peptide.

Means for Solving the Problems

As a result of an extensive study for accomplishing the above objects, the present inventor first made a gene library encoding with a diversity of not less than one hundred millions of peptides, incorporated each into a phagemid vector to allow each peptide to present at a top of g3p which was a phage coat protein, then added peptide surface display phages obtained in this way into cells, and selectively enriched the peptides having an ability to bind to a cell or penetrate into a cell by panning. Subsequently, the present inventor has found that a peptide having the ability to penetrate into the cell more efficiently than TAT peptide (Tat 48-60) can be created exhaustively and rapidly by adding into a cell, a fusion body of the selectively enriched peptide and a protein synthesis inhibitory factor (PSIF) that can not solely penetrate into the cell and evaluating cytoplasmic transfer (cell membrane permeability) using protein synthesis inhibition as an indicator, and have completed the present invention.

That is, the present invention relates to inventions shown as follows.

[1] At least one peptide selected from the group consisting of SEQ ID NOS:1 to 16.

[2] The peptide according to [1] above which is at least one selected from the group consisting of SEQ ID NOS:1, 5, 6, 7, 9, 10, 11, 15 and 16.

[3] The peptide according to [1] or [2] above adding at least one Cys residue to an N terminus and/or a C terminus of the amino acid sequence.

[4] A peptide conjugate linking the peptide according to any of [1] to [3] above and a physiologically active substance directly or indirectly through a crosslinker.

[5] A vaccine comprising the peptide according to any of [1] to [3] above or the peptide conjugate according to [4] above.

[6] A formulation for percutaneous absorption comprising the peptide according to any of [1] to [3] above or the peptide conjugate according to [4] above.

[7] Use of the peptide according to any of [1] to [3] above for introducing a physiologically active substance into a cell.

Effects of the Invention

According to the present invention, it is possible to highly efficiently introduce a polypeptide and/or a nucleic acid, etc. which is difficult to migrate into a cell when administered solely, into the cell.

Effects on prevention or treatment for or as a vaccine for various diseases can be anticipated by introducing the physiologically active substance such as polypeptides, nucleic acids and sugars which exhibit a biological activity when introduced into the cell, into the cell.

BEST MODES FOR CARRYING OUT THE INVENTION

Generally, biologically relevant substances such as peptides or proteins, nucleic acids and sugars are highly hydrophilic and are difficult to permeate through a cell membrane. When taking advantage of a physiological activity of such a substance, it is necessary to deliver the substance into a cell with keeping its physiological activity. If the biologically relevant substance is delivered into the cell through an endocytosis pathway, it is highly likely that the substance is metabolized and decomposed to lose its physiological activity. Therefore, it is preferable to deliver the biologically relevant substance through the pathway other than the endocytosis pathway.

Meanwhile recently, it has been found that a complex/fusion body of PTD (protein transduction domain) such as TAT peptide derived from HIV with a protein can pass through a blood brain barrier to migrate from blood into brain and can penetrate from an outside of the cell to an inside of the cell. Thus, attempts to apply PTD as a peptide DDS carrier have been noticed. For example, it has been greatly expected that proteins such as "intrabody" and "chaperon" capable of exerting therapeutic effects on cerebral nerve disease such as Alzheimer disease and Parkinson disease are attempted to apply as effective pharmaceuticals.

The peptide of the present invention is expected to be able to pass through the blood brain barrier and the cell membrane and exert great effects on improvement of biological activity expression and absorbability.

As described above, according to the present invention, it is possible to yield the cell permeable peptide having the higher cell permeability than TAT peptide (Tat 48-60). The present inventor performed the following experiments to show Examples more specifically in order to yield the cell permeable peptide of the present invention.

Phage Surface Display

Figure 1A:
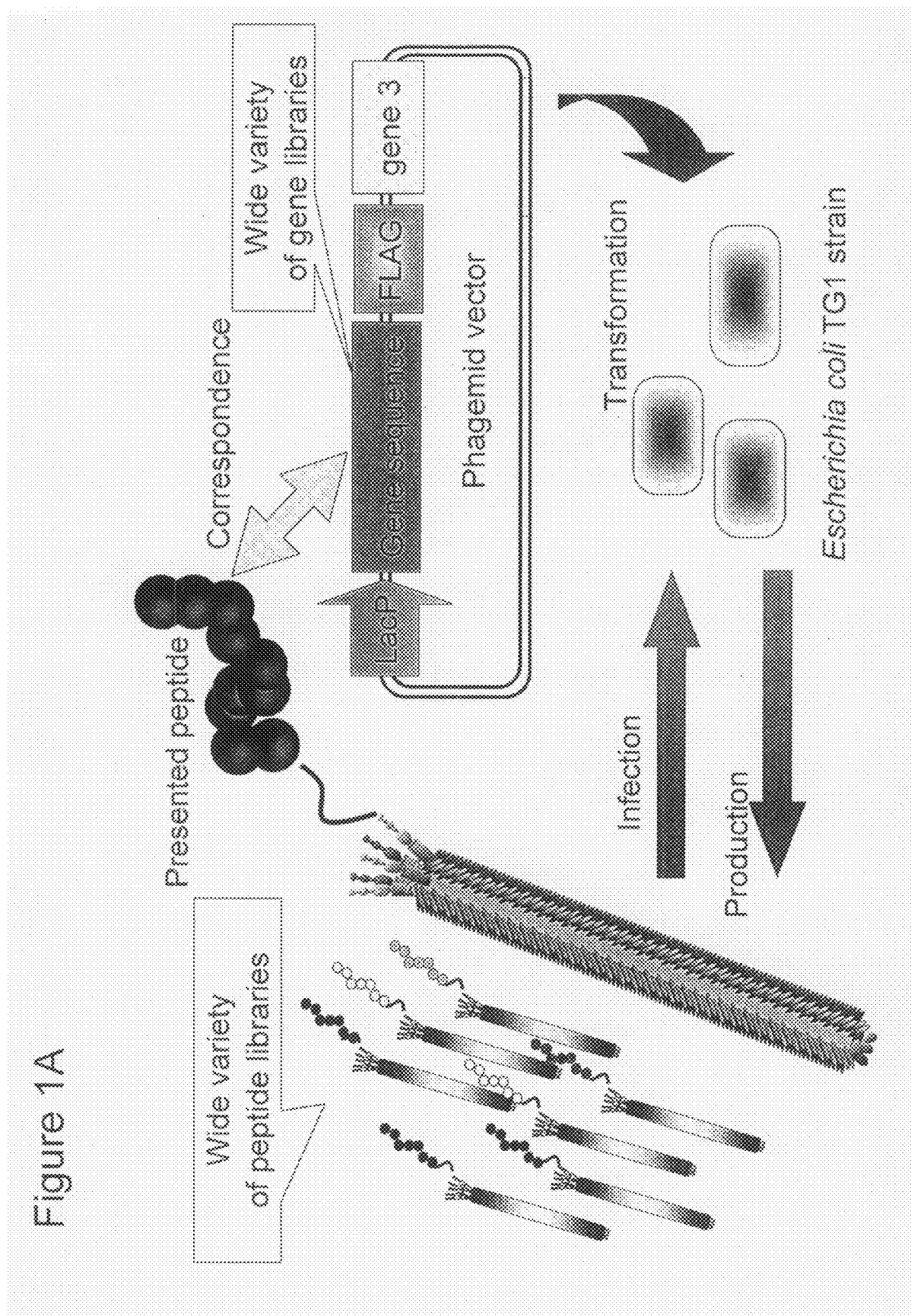
FIG. 1A is a view showing a principle of a phage surface display technique.
Figure 1B:
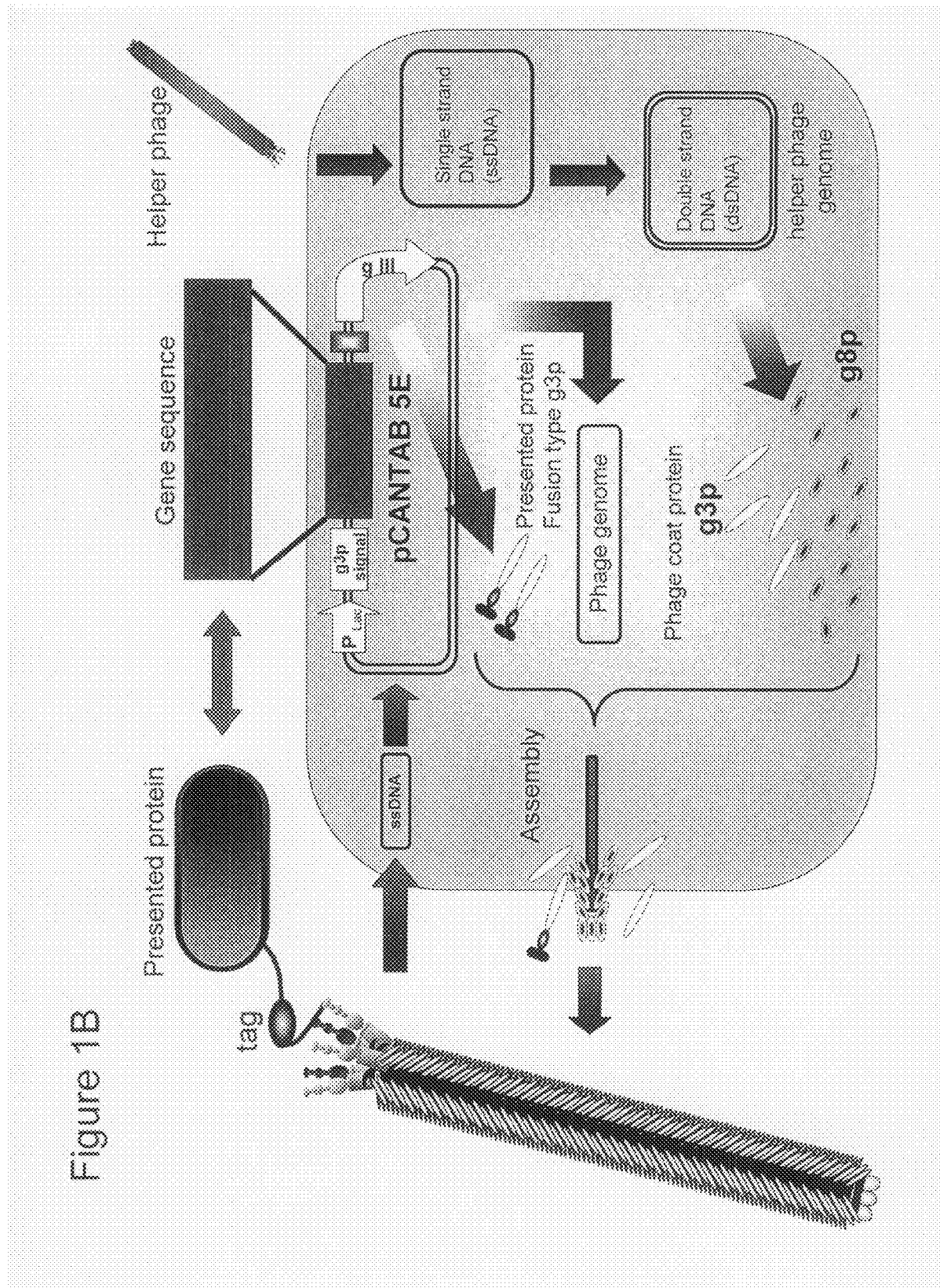
FIG. 1B is a view showing a principle of a phage surface display technique.
Figure 4:
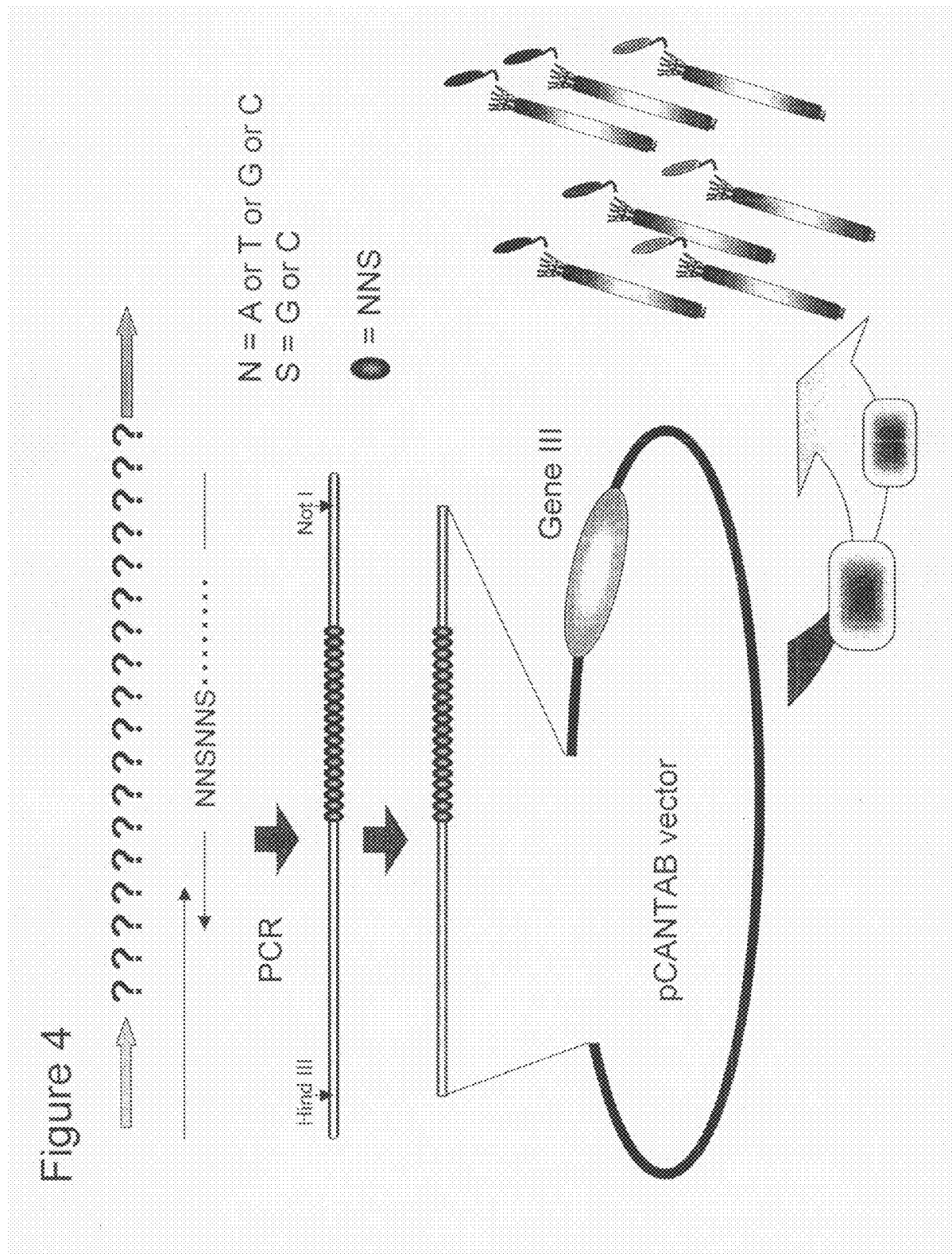
FIG. 4 is a view showing a principle for making a random 18 a.a. peptide library.
Figure 5:
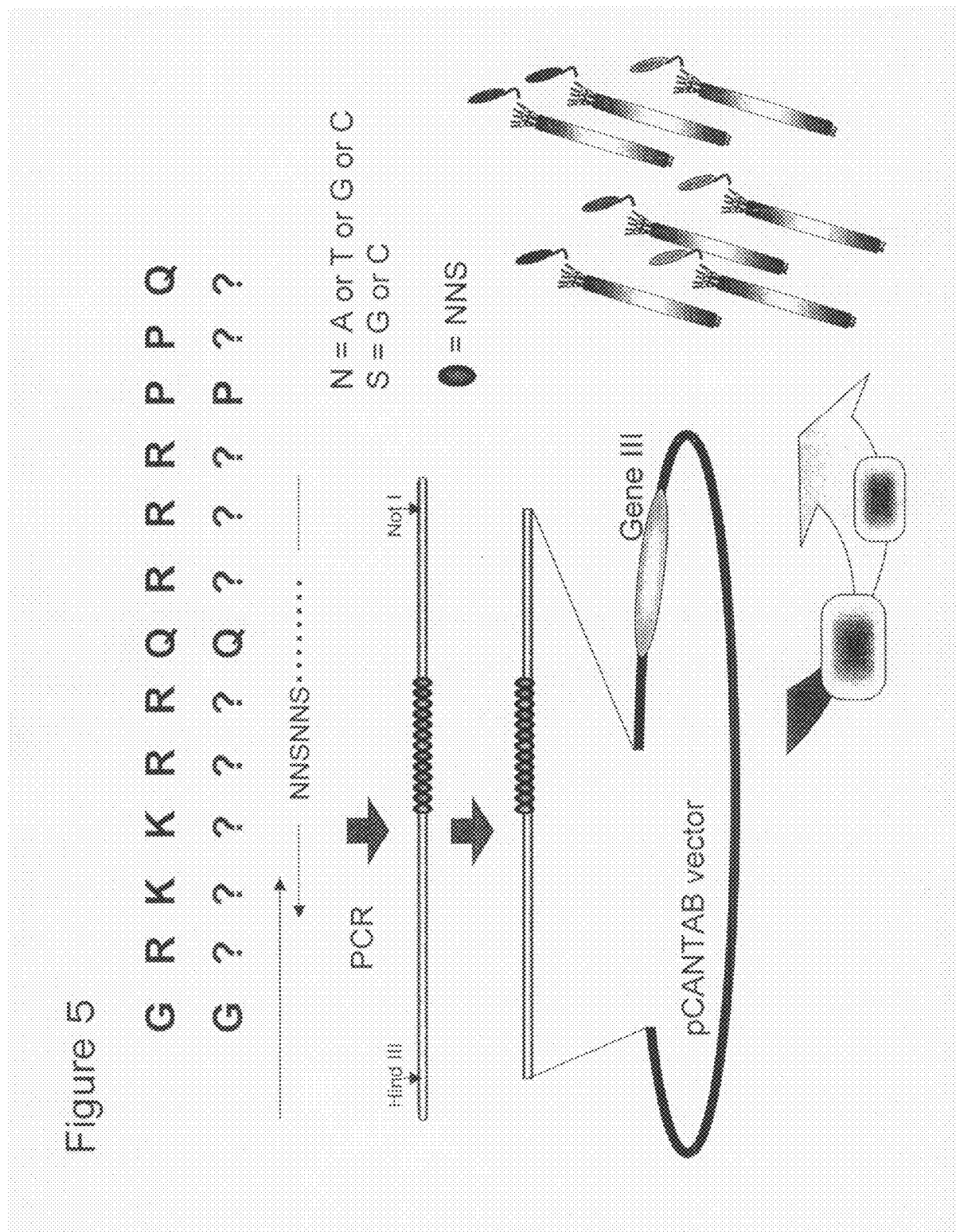
FIG. 5 is a view showing a principle for making a random Tat peptide library (peptide disclosed as SEQ ID NO: 17)

A "random 18 a.a. peptide library" (FIG. 4) where 18 amino acid residues had been randomly arranged, and a "TAT peptide library" (FIG. 5) where three amino acids (G at position 1, Q at position 7 and P at position 11) at a base point of α-helix had been fixed and other amino acid residues had been substituted in the TAT peptide (Tat 48-60) having a sequence of GRKKRRQRRRPPQ (SEQ ID NO:17) were made. PCR was performed using primers where an NNS sequence capable of encoding 20 amino acid residues had been introduced, and a PCR product was incorporated into a phagemid vector. A phage library where various types of peptides had been expressed at the top of g3p that was a phage minor coat protein was made by introducing this vector into *Escherichia coli* TG1 and infecting with a helper phage. DNA sequences of clones arbitrarily picked up from the library were analyzed. As a result, it was identified that the clone was composed of the independent clone. The phage surface display technique is a method publicly known to those skilled in the art (see FIG. 1).

Panning

Figure 2:
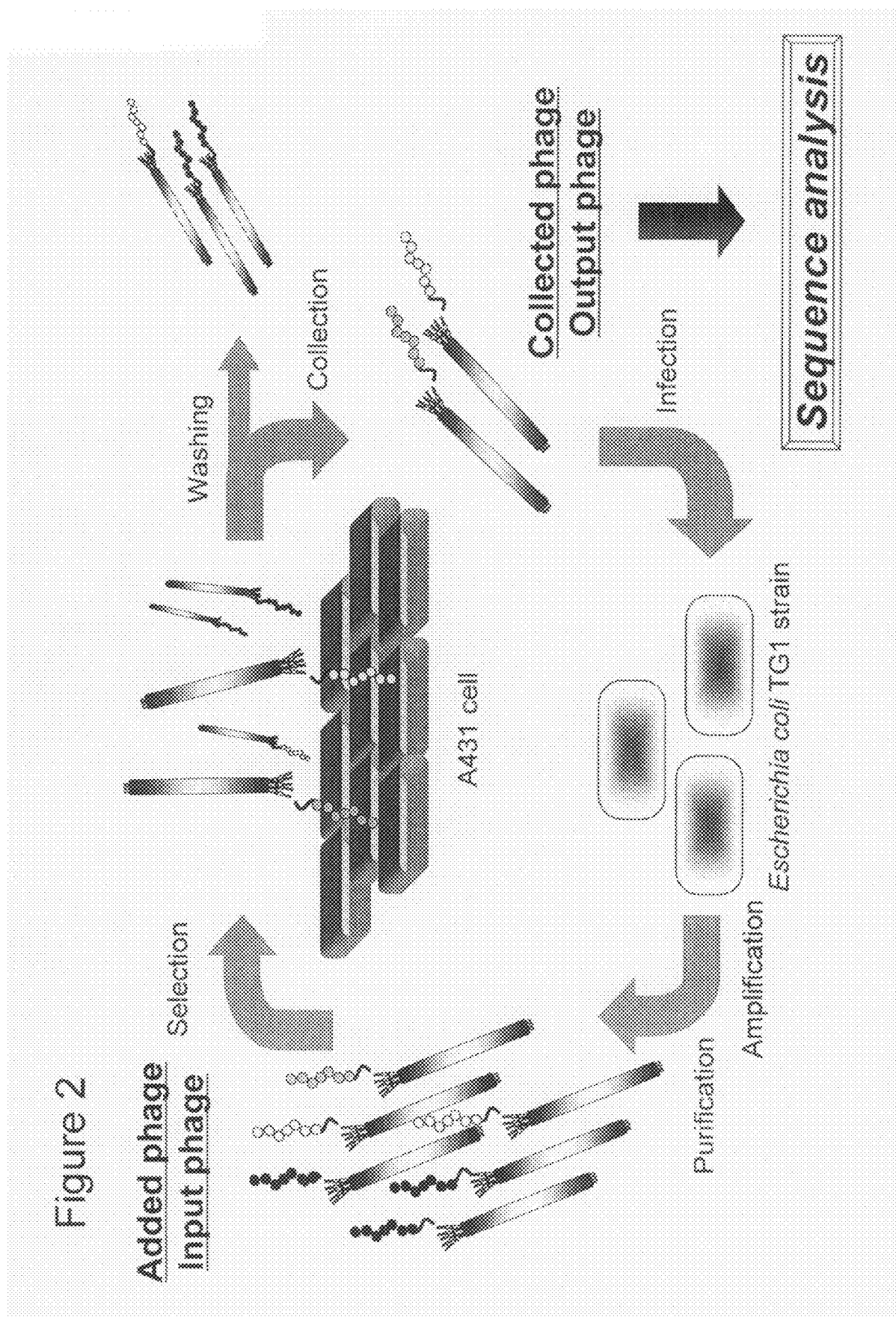
FIG. 2 is a view showing a principle of a cell panning.
Figure 3:
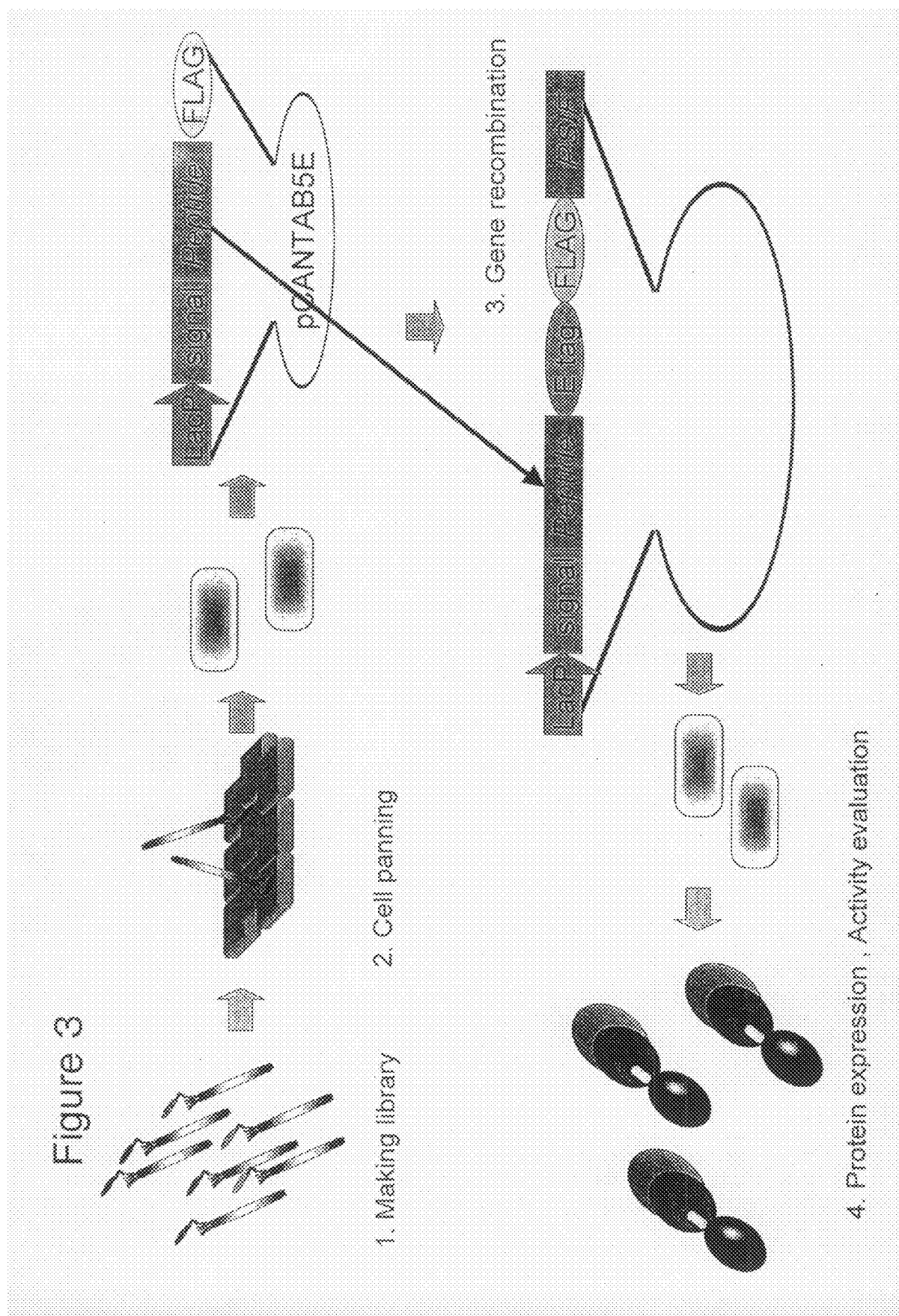
FIG. 3 is a view showing an outline of an experiment in Example 1.

In order to screen the peptides having an intracellular transfer ability, panning against A431 cells (human epidermal cells) was performed for each phage library made. It was confirmed that the clones having the ability to bind to the cell or penetrate into the cell were selectively enriched as the panning was repeated. PTD is generally characterized by abundantly containing basic amino acid residues. It was found that each clone enriched by the panning abundantly contained tryptophan (W) as well as the basic amino acid residues (see Table 1). The panning technique is the method publicly known to those skilled in the art (see FIG. 2; Nature Biotechnology Vol. 21, 546-552, 2003).

The phagemid vector for incorporating a library gene is not particularly limited, and includes, for example, pCANTAB5E (supplied from Amersham Bioscience) The method for making the phage displaying the peptide on its surface is known publicly (Applied and Environmental Microbiology Vol. 63, 263-269, 1997).

The yielded phage displaying the peptide on its surface is purified, and subsequently used for cell panning. The cell capable of being used for the cell panning is not particularly limited as long as it is the cell into which a physiologically active substance is penetrated with the cell permeable peptide of the present invention, and includes, for example, A 431 cell (human epidermal cell). When the human epidermal cell such as A431 cell is used, it is possible to select a polypeptide excellent in percutaneous absorption (permeability to the epidermal cell). When the other cell (e.g., organ or tissue other than skin) from mammalian animals including human is used in place of the human epidermal cell, it is possible to select a polypeptide excellent in absorbability or permeability to the other organ or tissue.

A number of the panning is not particularly limited, and is for example one to ten times, preferably two to eight times and more preferably three to five times. When the panning has been already performed sufficiently, a ratio of output phage/input phage is nearly constant.

Evaluation of Intracellular Transfer Ability of Peptide (Cytotoxic Test by PSIF)

Subsequently, using a fusion body of the peptide and PSIF (protein synthesis inhibitory factor) obtained by recombining each library gene in a PSIF-expressing vector, the intracellular transfer activity of the peptide was evaluated using the cytotoxicity by PSIF as an indicator. Since PSIF can not solely penetrate into the cell, no cytotoxicity is exhibited unless the peptide has the intracellular transfer activity. The screening was performed using a supernatant of the culture of *Escherichia coli* producing the fusion body of the peptide and PSIF. As a result, it can be confirmed that the clone having the ability to penetrate into the cell is selectively enriched as the panning is repeated. It was successful to yield many clones having a higher introduction efficiency than TAT peptide currently described to be the most excellent in introduction efficiency.

The present inventor have discovered the fact that no cell dies even if the protein synthesis inhibitory factor (PSIF) is added at a high concentration to the cell but the cell dies when the fusion body of PSIF and TAT is added to the cell, and have found from this fact that PSIF itself can not penetrate into the cell but PSIF can penetrate into the cell when fused with TAT.

That is, the protein synthesis inhibitory factor (PSIF) itself derived from a microbial cell can not solely penetrate into the cell, and thus, does not exhibit an inhibitory effect on protein synthesis at all. On the other hand, when a cytoplasmic transfer ability is imparted to PSIF by fusing/binding with PTD such as TAT (minimum 11-mer peptide), PSIF exerts the inhibitory effect on the protein synthesis for the first time.

PSIF (protein synthesis inhibitory factor) includes a protein synthesis inhibitory activity region of diphtheria toxin (GenBank; A04646) or *Pseudomonas* exotoxin (GenBank; K01397), and both are available.

Peptides of the Present Invention

According to the present invention, the peptide having the higher cell permeability than TAT peptide (Tat 48-60) is provided.

The peptide of the present invention has an amino acid sequence composed of 3 to 30, preferably 3 to 20 and more preferably 3 to 18 amino acid residues as a portion which exerts the cell permeability. As the number of the amino acid residues of the peptide is increased, the immunogenicity of the peptide tends to become high. Thus, a short peptide sequence is preferable when the function of the physiologically active substance which hardly penetrates the cell membrane is expressed in the cell. When the peptide is administered as a vaccine for inducing an immunity, an optional peptide involved in induction of the immunity may be linked. For example, when the peptide is administered as the vaccine by binding the peptide presented on the immune cell surface in order to induce the cellular immunity, the peptide may be longer.

Meanwhile, when the peptide of the present invention is introduced by linking to the physiologically active substance (e.g., peptides, proteins, polynucleotides, polysaccharides, glycoproteins, glycolipids) having no or poor cell permeability, the shorter peptide might be appropriate.

The "physiologically active substance" herein could be the substance capable of affecting the function or the state of the cell when introduced into the cell, and includes, for example, but is not limited to, nucleic acids, peptides, polypeptides, proteins, polysaccharides and glycoproteins.

In such a case, the physiologically active substance may be bound through an amide bond (peptide bond), an ester bond, a thioester bond, or the like so that it is cleaved with an enzyme (hydrolase such as peptidase and esterase) in the cell. Alternatively, since an intracellular environment is typically reductive, if the physiologically active substance to be introduced into the cell is bound through a disulfide bond, the physiologically active substance can be cleaved intracellularly to be liberated. Alternatively, a combination of the objective physiologically active substance and a particular substance (e.g., nucleic acid-polycation binding the peptide of the present invention, the peptide of the present invention binding an avidin—the physiologically active substance binding biotin, an antibody—an antigen binding the peptide of the present invention) can also be used.

The peptide of the present invention can permeate through the cell membrane of skin or gastrointestinal tract or tissues (muscle, subcutaneous, vascular endothelium, etc.) injected.

The "cell permeability" herein means a nature to permeate through the cell membrane to penetrate into the cell. Therefore, when the physiologically active substance is linked to the peptide of the present invention or made into a complex with the peptide of the present invention, the peptide can permeate together with the physiologically active substance through the cell membrane to penetrate into the cell.

"Being bound to the cell" herein refers to being simply bound to the cell surface. Meanwhile, "penetrating into the cell" refers to not only being bound to the cell surface but also further permeating through the cell membrane to penetrate into the cell.

A "target cell" herein is not particularly limited as long as it is the cell to be penetrated by the peptide together with the physiologically active substance, and include, for example, cells from various organs, e.g., vascular endothelial cells, mucosal epithelial cells, skin cells (keratinocytes) and muscular cells, and blood cells (lymphocytes, macrophages, T cells, dendritic cells and B cells).

The peptide of the present invention includes the polypeptide represented by any of SEQ ID NOS:1 to 16 and preferably any of SEQ ID NOS:1, 5, 6, 7, 9, 10, 11, 15 and 16. These sequences comprise polypeptides having one or more amino acid substitutions, deletions or additions as long as they keep the cell permeability.

As long as the modified peptide has the cell permeability, a degree, a position, and the like of the "deletion, substitution or addition of the amino acids" are not limited. The "cell permeability" in the present invention means that the physiologically active substance bound to the peptide of the present invention permeates through the cell membrane and is introduced into the cell.

As procedures for the substitution, addition or deletion of the amino acids, when performed via DNA encoding the peptide, for example, gene engineering techniques such as site-specific mutagenesis (Methods in Enzymology, 154, 350, 367-382 (1987)) and chemical synthesis procedures such as phosphate triester method and phosphate amidite method (J. Am. Chem. Soc., 89, 4801(1967)) can be exemplified. DNA can also be chemically synthesized by phosphoramidite method or triester method, and also be synthesized using commercially available automatic oligonucleotide synthesizer. A double strand fragment can be yielded from a chemically synthesized single strand product by synthesizing a complementary strand and annealing both strands under an appropriate condition, or adding the complementary strand together with an appropriate primer sequence using DNA polymerase. Furthermore, the peptide of the present invention can also be synthesized by solid phase synthesis method using a peptide synthesizer. The substitution/addition/deletion can be easily performed by changing the type of the protected amino acid when using the peptide synthesizer. It is also possible to introduce special amino acids such as D-amino acids and sarcosine (N-methylglycine).

Specific examples of the polypeptide (physiologically active substance) to be introduced into the cell include, but are not limited to, proteins (including enzymes) such as carbonic anhydrase, myoglobin, horseradish peroxidase, β-galactosidase, transcription factors having leucine zipper or zinc finger motif, apoptosis-inducing proteins such as Fas and p53, and adenosine deaminase, deletion of which induces diseases such as metabolic abnormality, and enzyme inhibitors (e.g., calpain inhibitor), genetic information expression regulatory factors (e.g., IκB, NFκB), and peptide hormones (insulin, calcitonin, etc.).

The polypeptide to be linked to the peptide of the present invention and be introduced into cell is not particularly limited, and includes arbitrary polypeptides. A molecular weight of the polypeptide is about 500 to 1,000,000, and preferably about 1,000 to 500,000. The types such as secretory proteins, membrane bound proteins and peptide hormones are not limited.

The peptide of the present invention may be linked with cysteine residue of the polypeptide to be introduced into the cell through an —SS— bond or may be linked with the polypeptide through an appropriate crosslinker when the peptide of the present invention has the cysteine residue or when at least one cysteine residue is introduced (insertion, addition or substitution) inside, or to the N terminus or the C terminus of the peptide of the present invention. It is possible to obtain the peptide conjugate where the protein or the polypeptide to be introduced into the N terminus or the C terminus (preferably the C terminus) of the peptide of the present invention has been directly linked by standard methods in which a polynucleotide (gene) encoding the peptide of the present invention and a polynucleotide encoding the polypeptide to be introduced are bound, preferably directly, which is then introduced into the vector and expressed in the host cell such as *Escherichia coli*. Likewise, the nucleic acid or the sugar can be linked through the appropriate crosslinker.

The crosslinker is not particularly limited as long as it is at least a bivalent crosslinker capable of binding the cell permeable peptide of the present invention to the protein or the polypeptide, or the nucleic acid or the sugar or the physiologically active substance having the low cell permeability to be introduced, and includes, for example, N-(6-maleimidecaproyloxy) succin-imide ester (EMCS).

It is preferable to further bind the Cys residue in a C terminal side by a mode of Cys or Gly-Cys and the Cys residue in an N terminal side by a mode of Cys or Cys-Gly in the cell permeable peptide of the present invention. An SH group in the Cys residue can be linked to the protein or the polypeptide to be introduced by addition reaction to a maleimide group in EMCS, or through the —SS— bond when the protein or the polypeptide to be introduced has the free SH group. When linked through the —SS— bond, the —SS— bond is reduced to liberate the unmodified protein or polypeptide in the cell. Thus, this is preferable.

The peptide library to be presented on the phage surface may be those where all amino acid residues are random or those where a part of TAT peptide remains original and other amino acid residues are random. For example, the TAT peptide library can be made by foxing three amino acids (G at position 1, Q at position 7 and P at position 11) at a base point of α-helix in the sequence of GRKKRRQRRRPPQ (SEQ ID NO:17) and randomly substituting the other amino acid residues.

Peptide Conjugate

The physiologically active substance to be bound to the peptide of the present invention is not particularly limited, and for example, is selected from the group consisting of nucleic acids, peptides, polypeptides, proteins, polysaccharides and glycoproteins. The physiologically active substance may be bound to any portion in the peptide of the present invention, but it is preferable to be bound to the C terminus or the N terminus, in particular bound to the C terminus because of easily making recombinants.

The peptide of the present invention is good in both percutaneous absorption and permucosal absorption, and thus is preferably used for topically administered agents, e.g., ointments, plasters, lotions, creams, inhales and nasal drops, and in particular tape formulations for the percutaneous absorption.

The present invention also relates to the vaccine comprising the peptide or the peptide conjugate of the present invention. Conventional vaccines potentiate the humoral immunity, i.e., enhance the production of an antigen specific antibody, and are effective for removal of viral particles released extracellularly, but are ineffective for the removal of infected cells which are causes of viral infection and cancer cells. It is required for treating the viral infection to enhance the cellular immunity. It is publicly known that the cellular immunity is enhanced by penetration of the antigen into the cell. Therefore, the peptide conjugate linking the peptide of the present invention to the antigen can place the antigen in the cell, and can be very useful as the vaccine.

In the present invention, a protective antigen which is the physiologically active substance to be introduced into a cell includes proteins derived from pathological microorganisms (bacteria, fungi, viruses, etc.), which become infection protective antigens of the microorganisms, mutant proteins which express specifically for cancer cells, or peptide fragments thereof keeping the immunogenicity, and additionally, all attenuated live microorganisms and killed microorganisms conventionally used as live vaccines and inactivated vaccines. The protein derived from the microorganism includes, for example, proteins derived from HIV, surface antigens from hepatitis B and C viruses and surface antigens from influenza virus. The mutant protein specific for the cancer cell includes canceration cell differentiation antigen proteins. The protective antigen may be used alone or in mixture of two or more.

A pharmaceutical composition comprising the antigen specific peptide conjugate of the present invention may be an oral agent or a parenteral agent, and may be, for example, a drug for external use. Specifically, for example, an ointment prepared by blending the protective antigen with an appropriate ointment base, or an adhesive tape formulation using an adhesive layer as a base by inoculating the protective antigen in the adhesive layer or embedding it in the adhesive layer, designed so that sustained release becomes possible is included.

In the case of the ointment, as the ointment base, for example, oil based bases such as Vaseline, paraffin, plastibase, silicon, plant oil and wax, emulsifier based bases such as hydrophilic ointments, hydrophilic Vaseline, purified lanoline and Eucerin, and water soluble bases such as macrogol are exemplified. If necessary, a preservative such as paraoxybenzoate ester may be added.

Percutaneous inoculation of the protective antigen can be performed by applying the ointment on skin epidermis. It is preferable to adjust the content of the protective antigen in the ointment so that an administered amount when typically applied is in the range of 0.1 μmol/cm$^2$ to 1 mmol/cm$^2$ per one antigen.

A particularly preferable aspect of the percutaneous inoculation of the protective antigen is the adhesive tape formulation (also referred to as a "tape formulation for percutaneous absorption") of the present invention, and this is attached on the skin epidermis. It is desirable that the adhesive tape formulation of the present invention is designed so that the protective antigen is appropriately slowly released simultaneously with that the protective antigen inoculated on the adhesive layer surface or embedded in the adhesive layer is stably present to an extent that the function of the original protective antigen is kept. It is also desirable that an adhesive force of this adhesive tape formulation is designed strongly to sufficiently adhere onto the epidermis. It is preferable that an adhesive used does not decrease or change the antigenicity of the protective antigen. The adhesive may be an acryl based polymer adhesive or a rubber based polymer adhesive as long as it satisfies the above condition. In particular, the adhesive suitably used includes the adhesive composed of a hydrophilic polymer.

Examples of the hydrophilic polymer include water soluble natural polymers such as gum acacia and carboxymethylcellulose, and polyvinyl pyrrolidone, polyvinyl alcohol, polymethoxyethyl acrylate and polyacrylic acid obtained by polymerizing water soluble monomers such as vinyl pyrrolidone, vinyl alcohol, 2-hydroxyethyl acrylate, 2-methoxyethyl acrylate and acrylic acid, and further copolymers of two or more of these water soluble monomers. In the range in which the hydrophilicity required in the present invention is not impaired, the adhesive may be adhesive polymers obtained by polymerizing hydrophobic monomers such as butyl acrylate and acrylic acid-2-ethylhexyl.

A hydrophilic or hydrophobic low molecular substance may be added to the adhesive layer in order to impart the more appropriate adhesiveness. The hydrophilic or hydrophobic low molecular substance includes liquid compounds having a high boiling point of 100 to 400° C. Specific examples thereof include polyvalent alcohol and sugar alcohol, and at that time, a reducing sugar which does not cause a browning reaction (Maillard chemistry) by reacting with the protein is preferably used. Polyvalent alcohol includes ethylene glycol, diethylene glycol, triethylene glycol, liquid polyethylene glycol, propylene glycol, dipropylene glycol and 1,1,1-trihydroxypropane and glycerine. The reducing sugar includes sorbitol, sorbitan, erythritol, xylitol and trehalose.

Polyoxyethylene glycel ether, polyoxypropylene sorbitol ether or polyoxyethylene sorbitan ether which is an ether type adduct of glycerine with ethylene glycol or propylene glycol may be used. The amount of the hydrophilic or hydrophobic low molecular substance to be added is in the range of 5 to 90% by weight relative to the amount of the adhesive which forms the adhesive layer.

In a flexible sheet support used for the tape formulation of the present invention, its material is not particularly limited as long as the material has a strength enough not to be broken upon handling, and for example, plastic films composed of polyethylene, polypropylene, polyester, polyamide, polycarbonate, polysulfone, polyvinyl chloride, polyether, polyurethane, ethylene-vinyl acetate copolymer, cellulose acetate or nitrocellulose are suitably used.

The adhesive tape formulation of the present invention is produced, for example, by adding a water dispersion or a water/alcohol mixture dispersion prepared to contain the protective antigen at required concentration to an aqueous solution or a water/alcohol mixture solution containing the above adhesive hydrophilic polymer and the hydrophilic low molecular substance, mixing and dispersing the mixture well, subsequently applying the mixture on the flexible sheet support at a constant thickness, and then drying at appropriate temperature in the range of 10 to 200° C. It is preferable that the drying temperature at that time is low as possible in order to prevent alteration of the content in the applied viscous dispersion, and the temperature range of 30 to 100° C. is typically employed. The adhesive layer of the adhesive tape formulation produced by this method contains the protective antigen at required concentration and evenly. All of or a part of the protective antigen is embedded in the formed adhesive layer, and consequently, the tape formulation is designed so that the protective antigen is appropriately slowly released. Another method for producing the adhesive tape formulation of the present invention includes the method in which first the adhesive tape containing no protective antigen is produced by directly adding the aqueous solution or the water/alcohol mixture solution containing the above adhesive hydrophilic polymer and the hydrophilic low molecular substance on the flexible sheet support at constant thickness and drying at appropriate temperature in the range of 10 to 200° C. or crosslinking if necessary, subsequently the water dispersion or the water/alcohol mixture dispersion prepared to contain the protective antigen at required concentration is applied onto the adhesive layer surface of the adhesive tape to have the required amount of the protective antigen, and the water or the alcohol is evaporated and dried. The adhesive tape formulation having an adhesive layer region containing the protective antigen and an adhesive layer region containing no protective antigen can be produced by appropriately combining the above two methods.

It is preferable that the adhesive tape formulation of the present invention is designed and prepared so that the protective antigen is contained in the amount of 0.1 $\mu mol/cm^2$ to 1 $mmol/cm^2$ per one antigen.

The present invention further relates to the use of the cell permeable peptide for introducing the physiologically active substance into the cell. The physiologically active substance includes at least one selected from the group consisting of nucleic acids, peptides, polypeptides, proteins, polysaccharides and glycoproteins.

EXAMPLES

The present invention will be described with reference to the following Examples, but the present invention is not limited thereto.

An outline of experiments is shown in FIG. 3.

Example 1

Preparation of Peptide Library

In order to make a "random 18 a.a. peptide library" where total 20 amino acid residues were randomly arranged and a "TAT peptide library" where parts of Tat peptide (13-mer; Tat 48-60) derived from a Tat protein of HIV were substituted with random amino acid residues, a gene library where random base sequences (NNS sequence; N=A/T/G/C, S=G/C) encoding total 20 amino acids had been arranged for 18 amino acid residues and a gene library where parts of base codons of the Tat peptide had been substituted with the NNS sequences were prepared using PCR method.

The random 18 a.a. peptide library was made by PCR with 35 cycles with pY03' FLAG (obtained by incorporating FLAG expression codon into pUC18 plasmid) as a template using primers oligo-1(5'-GATTACGCCAAGCTTTGGAGCCTTTTTTTTGGAGATTTTCAACGTGAAAAAATT ATTATTCGCAATTCCTTTAGTTGTTCCTTTCTATGCGGCCCAGCCGGCCATGGCC-3' (SEQ ID NO:18) and ligo-2(5'-CGGCGCACCTGCGGCCGCSNNSNNSNNSNNSNNSNNSNNSNNSNNSNNSNNSNNSNNSNNSNNSNNSNNSNNGGCCATGGCCGGCTGGGCCGCATAGAAAGG-3' (SEQ ID NO:19) by setting an annealing at 65° C. for one minute and an extension at 68° C. for one minute and using KOD-plus-DNA polymerase (Toyobo Co., Ltd.).

The TAT peptide library was made by PCR with 35 cycles with pY03' FLAG as the template using the primer oligo-1 (5'-GATTACGCCAAGCTTTGGAGCCTTTTTTTTGGAGATTTTCAACGTGAAAAAATTATTAT TCGCAATTCCTTTAGTTGTTCCTTTCTATGCGGCCCAGCCGGCCATGGCC-3' (SEQ ID NO:18) and the primer ligo-3(5'-CGGCGCACCTGCGGCCGCSNNSNNCGGSNNSNNSNNCTGSNNSNNSNNSNNSNN SNNACCGGCCATGGCCGGCTGGGCCGCATAGAAAGG-3' (SEQ ID NO:20) by setting the annealing at 65° C. for one minute and the extension at 68° C. for one minute and using KOD-plus-DNA polymerase These PCR products were purified using PCR purification kit (Qiagen companies). The resulting PCR product was treated with HindIII and NotI (Toyobo Co., Ltd.), and was ligated to a phagemid vector pY03' FLAG previously treated with HindIII and NotI using T4 ligase (Roche Diagnostics) at 16° C. for 16 hours. *Escherichia coli* TG1 (Stratagene, registered trade name) was previously cultured in 30 mL of 2YT medium (Invitrogen™ life technologies) until OD600=0.4, washed three times with MilliQ water, suspended in 200 μL, of 10% glycerol solution, and cooled. To resulting *Escherichia coli,* 10 μL of a purified ligated solution was added, and electroporation at 2.5 kV, 0.25 μF and 200 Q was performed using Gene purser (registered trade name) II (Bio-Rad Laboratories, Co., Ltd). Subsequently, the 2YT medium containing 2% glucose was added, and *Escherichia coli* was cultured for one hour. Then, a part of the culture was serially diluted with the 2YT medium containing 50 μg/mL of ampicillin (Sigma-Aldrich, Inc.) and 2% glucose, which was then seeded in CLONdisc (Clontech Laboratories, Inc.) and cultured overnight.

Sequence Analysis

The plasmid was collected using QIAprep (registered trade name) Miniprep kit (QIAGEN) from each clone arbitrarily selected from resulting colonies, and a sequence reaction was performed using DNA sequencing Kit (Applied Biosystems) and 5×Sequencing Buffer (Applied Biosystems). Subsequently, the product was purified using PERFORMA Gel Filtration Cartridge (Edge Bio Systems), and dried by heating under reduced pressure. The sequence was analyzed using ABI PRISM 310 (Applied Biosystems).

Preparation of Phage

By electroporation, Escherichia coli TG1 was transfected with a phagemid vector pCANTAB5E (Amersham Bioscience) in which the resulting library gene had been incorporated. The appropriate amount of the transfectant was seeded on an LB plate containing 50 μg/mL of ampicillin and 2% glucose, and cultured at 37° C. overnight. The 2YT medium containing 50 μg/mL of ampicillin and 2% glucose was added, all colonies were collected and cultured at 250 rpm until OD600=0.3. M13KO7 helper phage (Invitrogen™ life technologies) was added thereto, cultured at 110 rpm at 37° C. for 30 minutes and at 250 rpm at 37° C. for 30 minutes, and centrifuged at 2,000 rpm for 10 minutes. The 2YT medium containing 50 μg/mL of ampicillin and 100 μg/mL of kanamycin (Sigma Aldrich Inc.) was added to the resulting pellet, which was then cultured for 6 hours to prepare the phage displaying the peptide on its surface.

Purification of Phage

A TG1 culture solution containing phage particles was centrifuged at 2,000 rpm for 10 minutes, and a supernatant was collected. The supernatant was further centrifuged at 10,000 rpm for 15 minutes. To the resulting supernatant, ⅕ volume of 20% PEG-8,000 (Wako Pure Chemical Industries Ltd.) cooled with ice and 2.5 M NaCl (Wako Pure Chemical Industries Ltd.) were added and mixed vigorously. The solution was left stand on the ice for 2 to 3 hours, and then centrifuged at 15,000 rpm for 10 minutes to yield a phage pellet. The phage pellet was suspended in NTE Buffer (100 mM NaCl, 10 mM Tris, 1 mM EDTA), and filtrated through a filter using 0.45 μm Millex (registered trade name)—HV (Millipore) to make a purified phage solution.

Cell Panning

Using A431 cells (human epidermal cells), panning was performed for each library. A431 cells were seeded at $5.0 \times 10^5$ cells/well in a 6-well plate (NUNC™), and cultured at 37° C. under saturated vapor pressure and 5% carbon dioxide gas phase for 24 hours. The cells were washed three times with PBS, and then blocked using 2% bovine serum albumin (BSA) diluted with Opti-MEM (Invitrogen™ life technologies) at 37° C. for 2 hours. The purified phage was also blocked using an equal amount of 2% BSA at 4° C. for one hour. The phage after being blocked was added to A431 cells, and cultured 37° C. for 2 hours with shaking every 15 minutes. The cells were washed 20 times with PBS, then 1 mL of 50 mM HCl was added, and the cells were cultured at 4° C. for 10 minutes. This phage eluted solution was collected, 500 μL of 1 M Tris-HCl pH 8.0 was added, and a titer was measured using 50 μL thereof according to the following method. To the remaining phage solution, 4.5 mL of the 2YT medium containing 2% glucose was added, which was then infected again to Escherichia coli TG1. The infected Escherichia coli TG1 was amplified to produce the phage according to the above method for preparing the phage. The panning manipulation was repeated to make the 2nd, 3rd and 4th pannings.

Measurement of Titer

The phage solution serially diluted every 10 times was added to TG1 cultured in the 2YT medium containing 2% glucose until OD600=0.3, which was then cultured at 37° C. for one hour. The 2YT medium containing 50 μg/mL of ampicillin and 2% glucose was added to a part of the culture medium, which was then seeded in CLONdisc and cultured overnight. The titers of the input phage and the output phage were calculated by counting the number of the colonies in each serial dilution.

As described above, in order to create a new intracellularly transferring peptide, the random 18 a.a. peptide library where 18 amino acid residues had been randomly arranged and the TAT peptide library where partial amino acid residues of Tat peptide (Tat 48-60) had been substituted were made. PCR was performed using the primer where the NNS sequences capable of encoding 20 amino acid residues had been introduced, and the PCR product was incorporated in the phagemid vector. The phage library which expressed various types of peptides at the top of g3p which was the phage minor coat protein was made by introducing this vector into Escherichia coli TG1 and infecting the helper phage. The DNA sequence of the clone arbitrarily picked up from the library was analyzed. As a result, it was confirmed that the clone was composed of the independent clone.

In order to screen the peptide having the intracellular transfer ability, the panning against A431 cells (human epidermal cell) was performed for each phage library made. It was confirmed that the clone having the ability to bind to the cell or penetrate into the cell was selectively enriched as the panning was repeated. PTD is generally characterized by abundantly containing basic amino acid residues. It was found that each clone enriched by the panning abundantly contained tryptophan (W) as well as the basic amino acid residues.

Those arbitrarily picked up from the peptide library after the 4th panning were abundant in not only lysine (K), histidine (H) and arginine (R) which were basic amino acids but also tryptophan (W) which was a hydrophobic amino acid as shown in the following Table 1.

TABLE 1

| Clone | Sequence | Clone | Sequence |
|---|---|---|---|
| Tat random peptides randomly selected after 4th panning | | | |
| 1A (SEQ ID NO: 21) | GPMESLQAFWPPW | 15A (SEQ ID NO: 35) | GYFWYDQPWQPEQ |
| 2A (SEQ ID NO: 22) | GSSSWWQRWWPPW | 16A (SEQ ID NO: 36) | GRNHYIQRDNPVS |
| 3A (SEQ ID NO: 23) | GSSSWWQRWWPPWA | 17A (SEQ ID NO: 37) | GVFHVLQNAIPQY |
| 4A (SEQ ID NO: 24) | GVFLLKQVPQPSH | 18A (SEQ ID NO: 38) | GSSSWWQRWWPPW |
| 5A (SEQ ID NO: 25) | GSSSWWQRWWPPW | 19A (SEQ ID NO: 39) | GTMPNMQHHDPAR |
| 6A (SEQ ID NO: 26) | GRLWWLQLFEPGH | 20A (SEQ ID NO: 40) | GSSSWWQRWWPPW |
| 7A (SEQ ID NO: 27) | GLRKVPQSVPPDM | 21A (SEQ ID NO: 41) | GSSSWWQRWWPPW |

TABLE 1-continued

| Clone | Sequence | Clone | Sequence |
|---|---|---|---|
| 8A (SEQ ID NO: 28) | GSSSWWQRWWPPW | 22A (SEQ ID NO: 42) | GSSSWWQRWWPPW |
| 9A (SEQ ID NO: 29) | GHFLKPQVLRPTR | 23A (SEQ ID NO: 43) | GTRYLVQYLFPHL |
| 10A (SEQ ID NO: 30) | GQFMMRQYWPPVH | 24A (SEQ ID NO: 44) | GRPATQQGLTPAR |
| 11A (SEQ ID NO: 31) | GSSSWWQRWWPPW | 25A (SEQ ID NO: 45) | GYIGTYQQWNPPP |
| 12A (SEQ ID NO: 32) | GSSSWWQRWWPPW | 26A (SEQ ID NO: 46) | GSSSWWQRWWPPW |
| 13A (SEQ ID NO: 33) | GSSSWWQRWWPPW | 27A (SEQ ID NO: 47) | GSSSWWQRWWPPW |
| 14A (SEQ ID NO: 34) | GLLKYQQWASPLC | 28A (SEQ ID NO: 48) | GSSSWWQRWWPPW |
| 18-mer random peptides randomly selected after 4th panning | | | |
| 1B (SEQ ID NO: 49) | SLHNPHQCQNTMQRVYS | 16B (SEQ ID NO: 64) | QICALHERFMKNIINNCT |
| 2B (SEQ ID NO: 50) | NLNWQNWSSNNNPSLLRP | 17B (SEQ ID NO: 65) | RACNINNSHQAIVRATWF |
| 3B (SEQ ID NO: 51) | NWSAWPWNWRAWAMDLSG | 18B (SEQ ID NO: 66) | NWSAWPWNWRAWAMDLSG |
| 4B (SEQ ID NO: 52) | TNTVVFMNWENVWATLQSH | 19B (SEQ ID NO: 67) | GSFLLNRTRSSDHLWTRP |
| 5B (SEQ ID NO: 53) | TQKLMHSTTMHWDAHQDR | 20B (SEQ ID NO: 68) | SIQQARANGTTFRVTISN |
| 6B (SEQ ID NO: 54) | RTVQKREATMYTGHQFSD | 21B (SEQ ID NO: 69) | ADSAWMTLRYYPHQSWNH |
| 7B (SEQ ID NO: 55) | SSGANSFFNAIYDFLSNF | 22B (SEQ ID NO: 70) | ANYPWMYSYTWFTNRLMP |
| 8B (SEQ ID NO: 56) | IPSDCHTPRPATSLKLTS | 23B (SEQ ID NO: 71) | LTQMWPESTHSNRLHKIT |
| 9B (SEQ ID NO: 57) | AGQYTNVCWQNHRIWTNH | 24B (SEQ ID NO: 72) | SIVGAAHQNQGQL |
| 10B (SEQ ID NO: 58) | HHRSILNSGGQITKPYQN | 25B (SEQ ID NO: 73) | DRRSSQETKYTKYYTMPR |
| 11B (SEQ ID NO: 59) | NWSAWPWNWRAWAMDLSG | 26B (SEQ ID NO: 74) | NWSAWPWNWRAWAMDLSG |
| 12B (SEQ ID NO: 60) | LGGLTTTGNQPLANNHEW | 27B (SEQ ID NO: 75) | FSHPWRMTPNSTGTAIEH |
| 13B (SEQ ID NO: 61) | TTCMRSQNSWLDSRQRDW | 28B (SEQ ID NO: 76) | VTRNETDSPPPTHQYAHA |
| 14B (SEQ ID NO: 62) | WVQNPWSRWLTSGMSVFS | 29B (SEQ ID NO: 77) | STWMPRYNTRNAESVRYV |
| 15B (SEQ ID NO: 63) | RSHSIWALAPWWSKWLGF | 30B (SEQ ID NO: 78) | ANYPWMYSYTWFTNRLMP |

Recombination of PSIF Expression Vector

Figure 6:
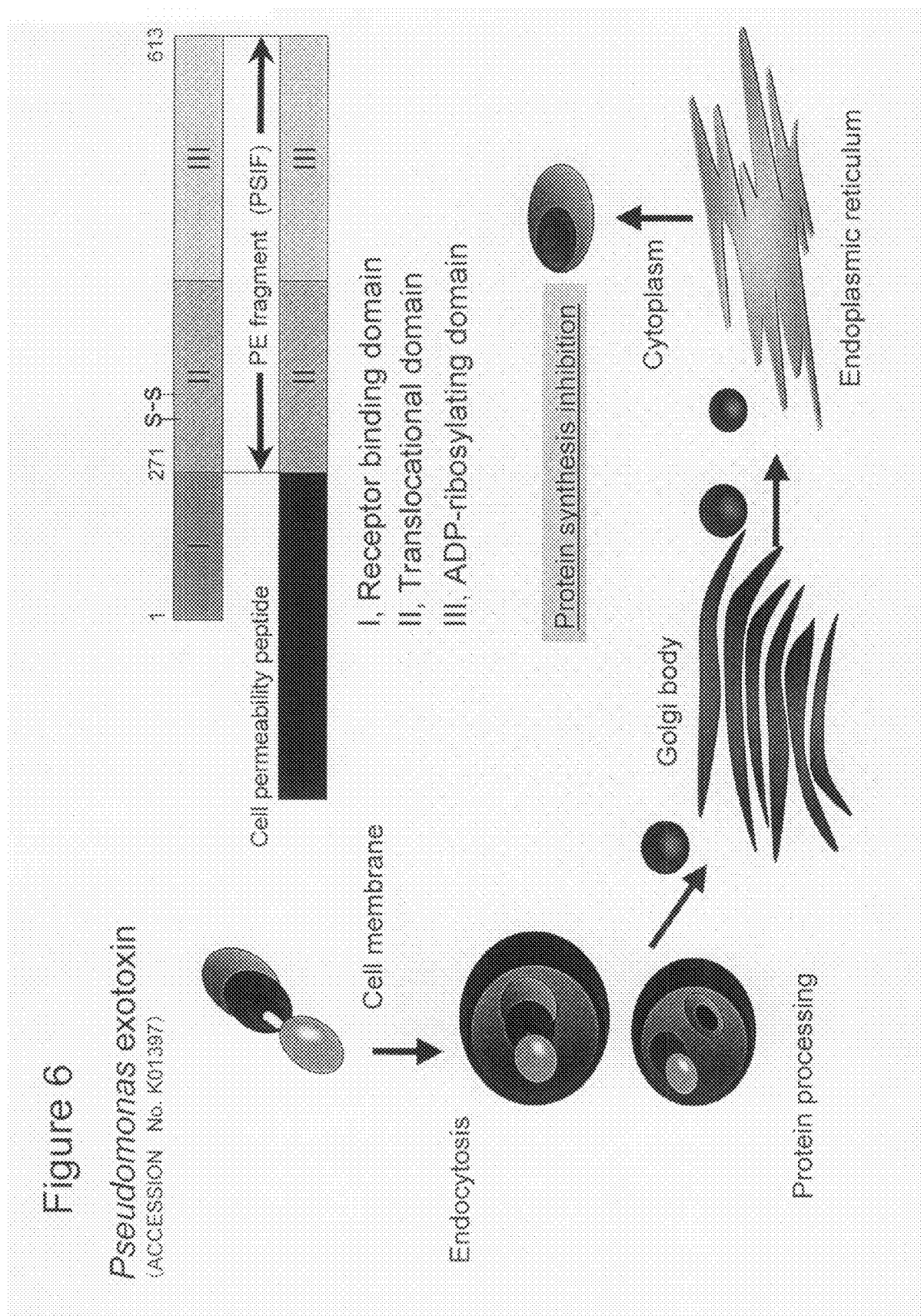
FIG. 6 is a view showing a structure and an action of *Pseudomonas* exotoxin (fragments were made by PCR) in cells.

The plasmids collected from the library (input) made and the libraries after the 2nd, 3rd and 4th panning were treated with NcoI (Toyobo Co., Ltd.) and NotI. A plasmid expressing the fusion body of the peptide and PSIF was constructed by incorporating the treated plasmid into PSIF expression vector pY7 (PSIF expression codons had been incorporated into pCantab5e) previously treated with NcoI and NotI using a ligation kit (Takara Shuzo Co., Ltd.). As PSIF (protein synthesis inhibitory factor), a protein synthesis inhibitory activity region of diphtheria toxin (GenBank; A04646) or Pseudomonas microbial cell exotoxin (GenBank; K01397) (FIG. 6) was utilized.

Preparation of Culture Supernatant Containing Fusion Body of Peptide and PSIF

The plasmid expressing the fusion body of the peptide and PSIF was introduced into TG1 by electroporation, and resulting colonies were randomly picked up into a 96-well plate (NUNC™) and cultured overnight. To a plate in which 100 μL of the 2YT medium containing 50 μg/mL of ampicillin and 2% glucose was newly added, 10 μL of the culture medium cultured overnight was added and cultured until OD600=0.4 to 0.5. The culture was centrifuged at 3,000 rpm for 20 minutes, the supernatant was removed, and 200 μL of the 2YT medium containing 1 mM IPTG (Sigma Aldrich Inc.) and 50 μg/mL of ampicillin was added to the plate, which was then cultured at 37° C. for 12 hours. The culture was centrifuged again at 3,000 rpm for 20 minutes, and the resulting supernatant was subjected to the following screening.

Evaluation of Intracellular Transfer Ability of Peptide (Cytotoxicity Test by PSIF; MTT Assay)

A431 cells diluted at $1.0 \times 10^4$ cells/well with Opti-MEM (Invitrogen™ life technologies) were seeded in a 96-well plate, and cycloheximide (Wako Pure Chemical Industries Ltd.) at a final concentration of 10 μg/mL was added thereto. Then, 5 μL of the culture supernatant made according to the above method was added, and the cells were cultured at 37° C. under the saturated vapor pressure and 5% carbon dioxide gas phase for 24 hours. Subsequently, 10 μL/well of 5 mg/mL of MTT (Wako Pure Chemical Industries Ltd.) solution was added, and further cultured at 37° C. for 4 hours. Then, 100 μL/well of 20% SDS (Wako Pure Chemical Industries Ltd., Osaka, Japan)/0.01 N HCl was added and the plate was left stand in a dark place for 4 hours. The intracellular transfer ability of the peptide was evaluated using the cytotoxicity by PSIF introduced into the cells by the peptide as the indicator by measuring absorbance using a microplate reader (Test wave length: 595 nm/Reference wave length: 655 nm).

Viability was calculated by making the viability in the group treated with the culture supernatant containing the fusion body of the TAT peptide (Tat 48-60) and PSIF 100%.

As described above, the intracellular transfer ability of the peptide was evaluated by recombining each library gene into PSIF (protein synthesis inhibitory factor) expression vector, using the fusion body of the peptide and PSIF and using the cytotoxicity by PSIF as the indicator. Since PSIF itself does not have the intracellular transfer ability, no cytotoxicity is exhibited unless the peptide has the intracellular transfer ability. As a result of performing the screening using the culture supernatant of *Escherichia coli* producing the fusion body of the peptide and PSIF, it was found that the clone having the ability to penetrate into the cell was selectively enriched as the panning was repeated. Furthermore, many clones having the higher introduction efficiency than TAT peptide described to be currently the most excellent in introduction efficiency were successfully obtained.

The yielded peptide sequences and the viability are shown below.

TABLE 2

Peptide sequences and cell viability when fusion body of peptide and PSIF was added

| SEQ ID NO | Sequence | Viability |
|---|---|---|
| 1: | GSNFFYQHRLPFS | about 45% |
| 2: | GLFNWLQLRPPSW | about 80% |
| 3: | GILLRNQVLPPQI | about 65% |
| 4: | RRRRNRTRRNRRRVR | about 93% |
| 5: | GIASNGQLPTPKT | about 35% |
| 6: | SGEHTNGPSKTSVRWVWD | about 35% |
| 7: | SMTTMEFGHSMITPYKID | about 45% |
| 8: | STHLQYHVNYTSRTVVSM | about 60% |
| 9: | QDGGTWHLVAYCAKSHRY | about 45% |
| 10: | MSDPNMNPGTLGSSHILW | about 30% |
| 11: | SPGNQSTGVIGTPSFSNH | about 45% |
| 12: | STAPGSLQEDILDSVPA | about 85% |
| 13: | SPTRPTHQGLLPVSNKYT | about 77% |
| 14: | YSSAYEWFNRYKQPYYEL | about 65% |
| 15: | SSGANYFFNAIYDFLSNF | about 35% |
| 16: | GTSRANSYDNLKSETLTQ | about 15% |
| 17: | GRKKRRQRRRPPQ | 100% |

The invention claimed is:

1. An isolated peptide selected from the group consisting of SEQ ID NOS:1 to 3 and SEQ ID NOS:5 to 16.

2. The peptide according to claim 1 which is at least one selected from the group consisting of SEQ ID NOS:1, 5, 6, 7, 9, 10, 11, 15 and 16.

3. The peptide according to claim 1 adding at least one Cys residue to an N terminus and/or a C terminus of said amino acid sequence.

4. A peptide conjugate linking the peptide according to claim 1 and a physiologically active substance directly or indirectly through a crosslinker.

5. A method for introducing a physiologically active substance into a cell by permeating the physiologically active substance through a cell membrane to penetrate into the cell comprising the steps of:
   a) attaching at least one peptide according to claim 1 to form a conjugate with the said physiologically active substance;
   b) contacting the conjugate with the cell membrane such that the physiologically active substance is introduced into the cell.

* * * * *

SEQUENCE LISTING

```
<160> NUMBER OF SEQ ID NOS: 78

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Asn Phe Phe Tyr Gln His Arg Leu Pro Phe Ser
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Leu Phe Asn Trp Leu Gln Leu Arg Pro Pro Ser Trp
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Gly Ile Leu Leu Arg Asn Gln Val Leu Pro Pro Gln Ile
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Arg Arg Asn Arg Thr Arg Arg Asn Arg Arg Arg Val Arg
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ile Ala Ser Asn Gly Gln Leu Pro Thr Pro Lys Thr
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Glu His Thr Asn Gly Pro Ser Lys Thr Ser Val Arg Trp Val
1               5                   10                  15

Trp Asp

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Met Thr Thr Met Glu Phe Gly His Ser Met Ile Thr Pro Tyr Lys
1               5                   10                  15

Ile Asp

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Thr His Leu Gln Tyr His Val Asn Tyr Thr Ser Arg Thr Val Val
1               5                   10                  15
```

Ser Met

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Asp Gly Gly Thr Trp His Leu Val Ala Tyr Cys Ala Lys Ser His
1               5                   10                  15

Arg Tyr

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Ser Asp Pro Asn Met Asn Pro Gly Thr Leu Gly Ser Ser His Ile
1               5                   10                  15

Leu Trp

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Pro Gly Asn Gln Ser Thr Gly Val Ile Gly Thr Pro Ser Phe Ser
1               5                   10                  15

Asn His

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Thr Ala Pro Gly Ser Leu Gln Glu Asp Ile Leu Asp Ser Val Pro
1               5                   10                  15

Ala

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Pro Thr Arg Pro Thr His Gln Gly Leu Leu Pro Val Ser Asn Lys
1               5                   10                  15

Tyr Thr

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ser Ser Ala Tyr Glu Trp Phe Asn Arg Tyr Lys Gln Pro Tyr Tyr
1               5                   10                  15

Glu Leu

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ser Gly Ala Asn Tyr Phe Phe Asn Ala Ile Tyr Asp Phe Leu Ser
1               5                   10                  15

Asn Phe

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Thr Ser Arg Ala Asn Ser Tyr Asp Asn Leu Lys Ser Glu Thr Leu
1               5                   10                  15

Thr Gln

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Arg Lys Lys Arg Arg Gln Arg Arg Arg Pro Pro Gln
1               5                   10

<210> SEQ ID NO 18
<211> LENGTH: 109
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gattacgcca agctttggag cctttttttt ggagattttc aacgtgaaaa aattattatt      60
cgcaattcct ttagttgttc ctttctatgc ggcccagccg gccatggcc               109

-continued

```
<210> SEQ ID NO 19
<211> LENGTH: 102
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: modified_base
<222> LOCATION: (50)..(51)
<223> OTHER INFORMATION: a, c, t, g, unknown or other
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: modified_base
<222> LOCATION: (56)..(57)
<223> OTHER INFORMATION: a, c, t, g, unknown or other
<220> FEATURE:
<221> NAME/KEY: modified_base
<222> LOCATION: (59)..(60)
<223> OTHER INFORMATION: a, c, t, g, unknown or other
<220> FEATURE:
<221> NAME/KEY: modified_base
<222> LOCATION: (62)..(63)
<223> OTHER INFORMATION: a, c, t, g, unknown or other
<220> FEATURE:
<221> NAME/KEY: modified_base
<222> LOCATION: (65)..(66)
<223> OTHER INFORMATION: a, c, t, g, unknown or other
<220> FEATURE:
<221> NAME/KEY: modified_base
<222> LOCATION: (68)..(69)
<223> OTHER INFORMATION: a, c, t, g, unknown or other
<220> FEATURE:
<221> NAME/KEY: modified_base
<222> LOCATION: (71)..(72)
<223> OTHER INFORMATION: a, c, t, g, unknown or other
```

```
<400> SEQUENCE: 19
cggcgcacct gcggccgcsn nsnnsnnsnn snnsnnsnns nnsnnsnnsn nsnnsnnsnn      60
snnsnnsnns nnggccatgg ccggctgggc cgcatagaaa gg                        102

<210> SEQ ID NO 20
<211> LENGTH: 90
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: modified_base
<222> LOCATION: (50)..(51)
<223> OTHER INFORMATION: a, c, t, g, unknown or other
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: modified_base
<222> LOCATION: (56)..(57)
<223> OTHER INFORMATION: a, c, t, g, unknown or other

<400> SEQUENCE: 20
cggcgcacct gcggccgcsn nsnncggsnn snnsnnctgs nnsnnsnnsn nsnnsnnacc      60
ggccatggcc ggctgggccg catagaaagg                                      90

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Pro Met Glu Ser Leu Gln Ala Phe Trp Pro Pro Trp
1               5                   10
```

```
<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ser Ser Ser Trp Trp Gln Arg Trp Trp Pro Pro Trp
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Ser Ser Ser Trp Trp Gln Arg Trp Trp Pro Pro Trp Ala
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Val Phe Leu Leu Lys Gln Val Pro Gln Pro Ser His
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ser Ser Ser Trp Trp Gln Arg Trp Trp Pro Pro Trp
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Arg Leu Trp Trp Leu Gln Leu Phe Glu Pro Gly His
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

```
Gly Leu Arg Lys Val Pro Gln Ser Val Pro Pro Asp Met
1               5                   10
```

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Gly Ser Ser Ser Trp Trp Gln Arg Trp Trp Pro Pro Trp
1               5                   10
```

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Gly His Phe Leu Lys Pro Gln Val Leu Arg Pro Thr Arg
1               5                   10
```

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Gly Gln Phe Met Met Arg Gln Tyr Trp Pro Pro Val His
1               5                   10
```

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Gly Ser Ser Ser Trp Trp Gln Arg Trp Trp Pro Pro Trp
1               5                   10
```

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Gly Ser Ser Ser Trp Trp Gln Arg Trp Trp Pro Pro Trp
1               5                   10
```

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic

```
                            peptide

<400> SEQUENCE: 33

Gly Ser Ser Ser Trp Trp Gln Arg Trp Trp Pro Pro Trp
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Leu Leu Lys Tyr Gln Gln Trp Ala Ser Pro Leu Cys
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Tyr Phe Trp Tyr Asp Gln Pro Trp Gln Pro Glu Gln
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Arg Asn His Tyr Ile Gln Arg Asp Asn Pro Val Ser
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Val Phe His Val Leu Gln Asn Ala Ile Pro Gln Tyr
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ser Ser Ser Trp Trp Gln Arg Trp Trp Pro Pro Trp
1               5                   10

<210> SEQ ID NO 39
<211> LENGTH: 13
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Thr Met Pro Asn Met Gln His His Asp Pro Ala Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ser Ser Ser Trp Trp Gln Arg Trp Trp Pro Pro Trp
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ser Ser Ser Trp Trp Gln Arg Trp Trp Pro Pro Trp
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Ser Ser Ser Trp Trp Gln Arg Trp Trp Pro Pro Trp
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Thr Arg Tyr Leu Val Gln Tyr Leu Phe Pro His Leu
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Arg Pro Ala Thr Gln Gln Gly Leu Thr Pro Ala Arg
1               5                   10
```

```
<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Tyr Ile Gly Thr Tyr Gln Gln Trp Asn Pro Pro Pro
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Ser Ser Ser Trp Trp Gln Arg Trp Trp Pro Pro Trp
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Ser Ser Ser Trp Trp Gln Arg Trp Trp Pro Pro Trp
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Ser Ser Ser Trp Trp Gln Arg Trp Trp Pro Pro Trp
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Leu His Asn Pro His Gln Cys Gln Asn Thr Met Gln Arg Val Tyr
1               5                   10                  15

Ser

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 50

Asn Leu Asn Trp Gln Asn Trp Ser Ser Asn Asn Pro Ser Leu Leu
1               5                   10                  15

Arg Pro

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Trp Ser Ala Trp Pro Trp Asn Trp Arg Ala Trp Ala Met Asp Leu
1               5                   10                  15

Ser Gly

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Asn Thr Trp Phe Met Asn Trp Glu Asn Val Trp Ala Thr Leu Gln
1               5                   10                  15

Ser His

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Gln Lys Leu Met His Ser Thr Thr Met His Trp Asp Ala His Gln
1               5                   10                  15

Asp Arg

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Thr Val Gln Lys Arg Glu Ala Thr Met Tyr Thr Gly His Gln Phe
1               5                   10                  15

Ser Asp

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic

```
                    peptide

<400> SEQUENCE: 55

Ser Ser Gly Ala Asn Ser Phe Phe Asn Ala Ile Tyr Asp Phe Leu Ser
1               5                   10                  15

Asn Phe

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Pro Ser Asp Cys His Thr Pro Arg Pro Ala Thr Ser Leu Lys Leu
1               5                   10                  15

Thr Ser

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Gly Gln Tyr Thr Asn Val Cys Trp Gln Asn His Arg Ile Trp Thr
1               5                   10                  15

Asn His

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His His Arg Ser Ile Leu Asn Ser Gly Gly Gln Ile Thr Lys Pro Tyr
1               5                   10                  15

Gln Asn

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Trp Ser Ala Trp Pro Trp Asn Trp Arg Ala Trp Ala Met Asp Leu
1               5                   10                  15

Ser Gly

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 60

Leu Gly Gly Leu Thr Thr Thr Gly Asn Gln Pro Leu Ala Asn Asn His
1               5                   10                  15

Glu Trp

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Thr Cys Met Arg Ser Gln Asn Ser Trp Leu Asp Ser Arg Gln Arg
1               5                   10                  15

Asp Trp

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Val Gln Asn Pro Trp Ser Arg Trp Leu Thr Ser Gly Met Ser Val
1               5                   10                  15

Phe Ser

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ser His Ser Ile Trp Ala Leu Ala Pro Trp Trp Ser Lys Trp Leu
1               5                   10                  15

Gly Phe

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Ile Cys Ala Leu His Glu Arg Phe Met Lys Asn Ile Ile Asn Asn
1               5                   10                  15

Cys Thr

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 65

Arg Ala Cys Asn Ile Asn Asn Ser His Gln Ala Ile Val Arg Ala Thr
1               5                   10                  15

Trp Phe

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 66

Asn Trp Ser Ala Trp Pro Trp Asn Trp Arg Ala Trp Ala Met Asp Leu
1               5                   10                  15

Ser Gly

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 67

Gly Ser Phe Leu Leu Asn Arg Thr Arg Ser Ser Asp His Leu Trp Thr
1               5                   10                  15

Arg Pro

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 68

Ser Ile Gln Gln Ala Arg Ala Asn Gly Thr Thr Phe Arg Val Thr Ile
1               5                   10                  15

Ser Asn

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 69

Ala Asp Ser Ala Trp Met Thr Leu Arg Tyr Tyr Pro His Gln Ser Trp
1               5                   10                  15

Asn His

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Ala Asn Tyr Pro Trp Met Tyr Ser Tyr Thr Trp Phe Thr Asn Arg Leu
1               5                   10                  15

Met Pro

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Thr Gln Met Trp Pro Glu Ser Thr His Ser Asn Arg Leu His Lys
1               5                   10                  15

Ile Thr

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Ile Val Gly Ala Ala His Gln Asn Gln Gly Gln Leu
1               5                   10

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Arg Arg Ser Ser Gln Glu Thr Lys Tyr Thr Lys Tyr Tyr Thr Met
1               5                   10                  15

Pro Arg

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asn Trp Ser Ala Trp Pro Trp Asn Trp Arg Ala Trp Ala Met Asp Leu
1               5                   10                  15

Ser Gly

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 75

Phe Ser His Pro Trp Arg Met Thr Pro Asn Ser Thr Gly Thr Ala Ile
1               5                   10                  15

Glu His

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Val Thr Arg Asn Glu Thr Asp Ser Pro Pro Thr His Gln Tyr Ala
1               5                   10                  15

His Ala

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Thr Trp Met Pro Arg Tyr Asn Thr Arg Asn Ala Glu Ser Val Arg
1               5                   10                  15

Tyr Val

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Asn Tyr Pro Trp Met Tyr Ser Tyr Thr Trp Phe Thr Asn Arg Leu
1               5                   10                  15

Met Pro
```